US007968558B2

(12) United States Patent
Giordani et al.

(10) Patent No.: US 7,968,558 B2
(45) Date of Patent: Jun. 28, 2011

(54) AMIDINE DERIVATIVES OF 2-HETEROARYL-QUINAZOLINES AND QUINOLINES; POTENT ANALGESICS AND ANTI-INFLAMMATORY AGENTS

(75) Inventors: Antonio Giordani, Pavia (IT); Stefano Mandelli, Casatenovo (IT); Simona Zanzola, Milan (IT); Francesca Tarchino, Varazze (IT); Gianfranco Caselli, Milan (IT); Teresa Simonetta Fiorentino, Monza (IT); Silvio Mazzari, Padua (IT); Francesco Makovec, Lesmo (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 0 days.

(21) Appl. No.: 12/376,066

(22) PCT Filed: Jul. 31, 2006

(86) PCT No.: PCT/EP2006/064841
§ 371 (c)(1),
(2), (4) Date: May 6, 2009

(87) PCT Pub. No.: WO2008/014815
PCT Pub. Date: Feb. 7, 2008

(65) Prior Publication Data
US 2009/0227609 A1 Sep. 10, 2009

(51) Int. Cl.
*A61K 31/517* (2006.01)
(52) U.S. Cl. .................... 514/266.1; 544/283
(58) Field of Classification Search .............. 544/283
See application file for complete search history.

(56) References Cited

FOREIGN PATENT DOCUMENTS
EP 1 571 142 A1 9/2005

OTHER PUBLICATIONS

Morissette et al. "High-throughput crystallization: polymorphs, salts, co-crystals and solvates of pharmaceutical solids." 2004, Advanced Drug Delivery Reviews, 56, 275-300.*
West, Anthony R., Solid State Chemistry and its Applications, Wiley, New York, 1988, pp. 358 and 365.*
Lowell O. Randall et al.; A Method for Measurement of Analgesic Activity on Inflamed Tissue; Department of Pharmacology Hoffman-La Roche, Inc.; CX 1; No. 4; 1957; p. 409.
C.J. Woolf, A., et al.; Cytokines, nerve growth factor and inflammatory hyperalgesia: the contribution of tumor necrosis factor; Birtish Journal of Pharmacology; vol. 121, pp. 417-424; 1997.
Arthur Gomtsyan et al.; Novel Transient Receptor Potential Vanilloid 1 Receptor Antagonists for the Treatment of Pain: Structure-Activity Relationships for Ureas with Quinoline, Isoquinoline, Quinazoline, Phthalazine, Quinoxaline, and Cinnoline Moieties; Journal of Medicinal Chemistry; vol. 48 (3), pp. 744-752, 2005.
Dajie Li et al.; Nitroarylastannanes as Synthons for the Preparation of Phenanthridine and Benzo[i]phenanthridine Derivatives; The Journal of Organic Chemistry; vol. 65(9); pp. 2802-2805; 2000.
Steinar Hunskaar et al.; The formalin test in mice: dissociation between inflammatory and non-inflammatory pain; Pain, vol. 30, pp. 103-114; 1987.
Reza Sharif Naeini et al.; Remodeling of spinal nociceptive mechanisms in an animal model of monoarthritis; European Journal of Neuroscience, vol. 22, pp. 2005-2015, 2005.
B.J. Broughton et al.; Antiallergic activity of 2-phenyl-8-azapurin-6-ones; Journal of Medicinal Chemistry; vol. 18(11), pp. 1117-1122; 1975.
H.O.J. Collier et al.; The abdominal constriction response and its suppression by analgesic drugs in the mouse; British Journal Pharmac, Chemother.; vol. 32, pp. 295-310; 1968.
Cheryl L. Stucky et al.; Mechanisms of Pain; From the Academy; vol. 98, No. 21; pp. 11845-11846; Oct. 9, 2001.
Enzo Cereda et al.; Synthesis and biological evaluation of new antimuscarinic compounds with amidine basic centers. A useful bioisosteric replacement of classical cationic heads; Journal of Medicinal Chemistry; vol. 33 No. 8; pp. 2108-2113; 1990.
Katharine Walker et al.; Animal models for pain research; Molecular Medicine Today; vol. 5, p. 319, Jul. 1999.
C. Courteix, et al.; Streptozocin-induced diabetic rats: behavioural evidence for a model of chronic pain; Elsevier Science Publishers; vol. 53, pp. 81-88, 1993.
F.D. Bellamy, Selective Reduction of Aromatic Nitro Compounds with Stannous Chloride in Non Acidic and Non Aqueous Medium; Tetrahedron Letter, vol. 25, No. 8, pp. 839-842, 1984. Masanori Kosugi et al.; Preparation of Aryltributyltin Having Electron-withdrawing Group by Palladium Catalyzed Reaction of Hexabutylditin with Aryl Iodide; The Chemical Society of Japan; vol. 56, pp. 3855-3856, 1983.

(Continued)

*Primary Examiner* — James O Wilson
*Assistant Examiner* — Brian McDowell
(74) *Attorney, Agent, or Firm* — Sughrue Mion, PLLC

(57) ABSTRACT

The present invention concerns novel amidines derivatives of 2-heteroaryl-quinazoline and quinolines of general formula (I), to a process for their preparation, to their pharmaceutical compositions and to the use of these compounds, salts and solvates thereof, along with the corresponding pharmaceutical compositions, for the treatment of pain and inflammatory disorders. Compounds of this invention are extremely potent analgesics, suitable for the treatment of both inflammatory and neuropathic pain. Particularly for the treatment of neuropathic pain the compounds of the invention have been proved largely superior to the standards currently in the clinical use. These compounds are not acting through inhibition of COX or NOS enzymes but are effective in inhibiting inflammatory cytokine production induced by inflammatory stimuli.

Formula (I)

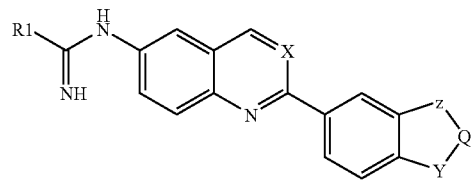

3 Claims, No Drawings

OTHER PUBLICATIONS

Mercedes Amat et al.; Palladium (0)-Catalyzed Heteroarylation of 2-and 3-Indolylzinc Derivatives. An Efficient General Method for the Preparation of (2-Pyridyl)indoles and Their Application to Indole Alkaloid Synthesis; The Journal of Organic Chemistry; vol. 62, No. 10, pp. 3158-3175; May 16, 1997.

S.T. Meller et al.; The Possible Role of Glia in Nociceptive Processing and Hyperalgesia in the Spinal Cord of the Rat; Neuropharmacology, vol. 33, No. 11, pp. 1471-1478, 1994.

Frances V. Abbott et al.; The formalin test: scoring properties of the first and second phases of the pain response in rats; Elsevier Science; vol. 60; pp. 91-102; 1995.

Barry G. Shearer et al.; S-2-Naphthylmethyl Thioacetimidate Hydrobromide: A new odorless Reagent for the Mild Synthesis of Substituted Acetamidines; Tetrahedron Letter, vol. 38, No. 2, pp. 179-182, 1997.

Dennis G. Hall; Boronic Acids; Preparation and Applications in Organic Synthesis and Medicine; Wiley-VCH Verlag GmbH & Co. KGaA; 2005.

* cited by examiner

AMIDINE DERIVATIVES OF 2-HETEROARYL-QUINAZOLINES AND QUINOLINES; POTENT ANALGESICS AND ANTI-INFLAMMATORY AGENTS

The present invention is directed to novel amidines of 2-heteroaryl-quinazoline and quinolines, to a process for their preparation, to their pharmaceutical compositions and to the use of such compounds and their pharmaceutical compositions for the treatment of pain and inflammatory related disorders.

BACKGROUND

Despite intensive research on the neurobiological mechanisms of chronic pain, this therapeutic area remains one of the least satisfactorily covered by current drugs. Over one-third of the world's population suffers from persistent or recurrent pain, and untreated pain may become self-perpetuating, because pain has immunosuppressive effects that leave patients susceptible to subsequent diseases (C. L. Stuky, Mechanisms of Pain, PNAS, 2001, 98, 11845). Pain is defined by the International Association for the Study of Pain (IASP, Classification of chronic pain, $2^{nd}$ Edition, IASP Press, 2002, 210) as "an unpleasant sensory and emotional experience associated with actual or potential tissue damage". Even though pain is always subjective, its causes or syndromes can be divided into two categories, physiological pain and pathological or clinical pain. Physiological pain is acute and has a protective role that warns of potential tissue damage, while pathological pain is usually chronic. Pathological pain can be mainly divided into inflammatory pain, a kind of pain more related to peripheral tissue damage/inflammation, and neuropathic pain.

Neuropathic pain refers clinically to a group of chronic pain syndromes. These syndromes share the common feature that they are caused by an initial nerve damage which subsequently results in an abnormal sensory processing in the central and peripheral nervous system. Neuropathic pain conditions are the consequence of a number of diseases, for instance diabetes, cancer, amputees, multiple sclerosis.

Inflammatory pain is affecting hundreds of millions of people in the world. Although arthritis (being rheumatoid arthritis and osteoarthritis the most common form of arthritis) is defined as inflammation of the joint, the primary feature with which patients present in the clinic is chronic pain; even though arthritis is not the only pathology which can give rise to chronic pain, it is rather common and quite representative of this kind of pain.

Peripheral sensitization and central sensitization are two major mechanisms underlying the generation of pathological pain. When tissue damage occurs, an inflammatory response develops that triggers mechanisms in both the nervous and the immune system. This results in an ongoing painful state. During tissues injury and inflammation, sensitizing agents such as pro-inflammatory prostaglandins ($PGE_2$), 5-HT, bradykinin, histamine, ATP, cytokines are released from inflammatory cells and nerve terminals. These mediators evoke activation of specific ion channels through the excitation of peripheral nociceptive neurons, involving activation of intracellular kinases, and resulting in peripheral sensitization. Activation of peripheral nociceptors also results in an activity or use dependent neuronal plasticity in the CNS. This plasticity modifies the performance of nociceptive pathway by enhancing and prolonging the responses to subsequent peripheral stimuli. These changes in the spinal cord, as well as in the brain are referred to central sensitization. Central sensitization plays a major role in maintaining elevated pain sensitivity and it is responsible for the pain produced after injury by normally innocuous low threshold afferent inputs. A so complex mechanism for pain induction and control can explain why the treatment of pain conditions has not found yet a satisfactory pharmacological solution.

Opiate drugs such as morphine are well known for their ability to produce potent analgesia as well as unwanted side effects, such as tolerance, physical dependence, respiratory suppression and constipation. In order to identify new agents for the clinical management of pain, several alternate pharmacological approaches have been carried out in the last decade, for example COX-2 inhibitors, displayed a good efficacy in the treatment of inflammatory pain, but lacked effectiveness in the treatment of neuropathic pain, in addition for COX-2 inhibitors undesirable life threatening side-effects were recently highlighted.

The available analgesics for the treatment of neuropathic pain, for instance some tricyclic antidepressant (e.g.: Amitriptyline) and a few antiepileptic drugs (e.g. gabapentin, lamotrigine, and carabamazepine) are effective in some patients, however there is still a large need for efficient drugs for neuropathic pain treatment.

DESCRIPTION OF THE INVENTION

The present invention comprises a new class of compounds, amidine derivatives of 2-heteroaryl quinazolines and quinolines of Formula (I), useful in therapy especially for the treatment of various pain conditions such as chronic pain, neuropathic pain, acute pain, cancer pain, pain caused by arthritis and visceral pain.

Compounds of the invention are also endowed with anti-inflammatory properties acting on the expression and cellular production of several pro-inflammatory mediators such as $PGE_2$ and cytokines, thus can be useful pharmacological agents for the treatment of arthritis, rheumatoid arthritis and osteoarthritis, intestinal inflammatory conditions such as ulcerative colitis and Chron's disease.

Compounds of Formula (I):

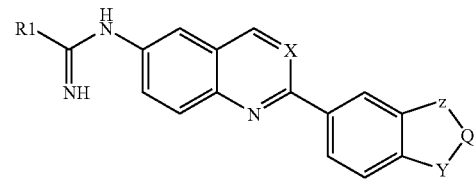

wherein:
X is independently selected from a carbon or a nitrogen atom;
Z and Y are independently selected from an oxygen atom (—O—), a sulphur atom (—S—), or the groups: —$SO_2$—, —$CH_2$—, —$CHR_2$—, —CH=, —$CR_2$=, —NH—, —N=;
Q is independently selected from the groups: —$CH_2$—, $CHR_2$—, —CH=, —$CR_2$=, —$CH_2$—$CH_2$—, —$CHR_2$—$CH_2$—;
provided that the combination of Y, Z, Q groups give rise to a benzocondesed hexa-atomic or penta-atomic heterocycles, preferably selected from 1,3-benzodioxole, 1,3-benzodithiol, benzofuran, 2,3-dihydrobenzofuran, benzothiophene, 2,3-dihydrobenzothiophene, 2,3-dihydrobenzothiophene S,S-dioxide, indole, 2,3-dihydroindole, benzimidazole, benzoxazole, benzothiazole, 2H-3,4-dihydrobenzopyran, 2H-3,4- dihydrobenzo-thiopyran, 2H-3,4-dihydrobenzothiopyran S,S-dioxide, [1,4]-benzodioxine, 2,3-dihydro-[1,4]-benzodioxine (1,4-benzodioxan), 1,4-benzothiazine, 2,3-dihydro-[1,4]-benzothiazine, 2,3-dihydro-[1,4]-benzothiazine S,S-dioxide, [1,4]-benzoxazine and 2,3-dihydro-[1,4]-benzoxazine;

$R_1$ is independently selected from $C_1$-$C_4$ alkyl or $C_1$-$C_4$ cycloalkyl; the $C_1$-$C_4$ alkyl group being a linear or branched, saturated or unsaturated, hydrocarbon chain; the $C_1$-$C_4$ cycloalkyl group being a cyclic $C_1$-$C_4$ hydrocarbon ring, optionally substituted with not more than two methyl or ethyl groups;

$R_2$ is independently selected from $C_1$-$C_4$ alkyl, alkoxy (—$OR_1$), phenyl or substituted phenyl, benzyl or substituted benzyl; the substituted phenyl herein being preferably a phenyl bearing one or two substituents independently selected from fluorine, chlorine, bromine, cyano, nitro, methyl, trifluoromethyl; the substituted benzyl being preferably a benzyl group where the phenyl is substituted with one or two substituents independently selected from fluorine, chlorine, bromine, cyano, nitro, methyl, trifluoromethyl.

According to this invention the compounds of Formula (I) may be used as the free base or as a pharmaceutically acceptable salt thereof, or as a solvate or hydrate form of such salt.

The salts of the compounds of Formula (I) are pharmaceutically acceptable addition salts with inorganic and organic acids. Representative not limiting examples of inorganic salts are: hydrochloride, hydrobromide, hydrogensulphate and sulphate. Representative not limiting examples of organic salts are: maleate, fumarate, oxalate, methanesulfonate, succinate, ascorbate, tartrate.

For compounds of Formula (I), tautomers are possible, the present invention is also directed to all possible tautomers of these compounds. p In another embodiment this invention provides methods for the preparation of compounds of Formula (I).

In a further embodiment this invention provides pharmaceutical compositions for compounds of Formula (I), useful for the treatment of pain and inflammatory disorders as discussed above. Within the scope of the present invention the term pharmaceutical composition (drug product) refers to any oral, parenteral or topical dosage form, suitable for the treatment of the above pathologies, that contains an effective amount of at least one of the active pharmaceutical ingredients (drug substances), compounds of Formula (I), its salts or solvates, and a pharmaceutically acceptable carrier, excipients or diluents as defined below, for oral, parenteral or topic administration.

Representative not limiting examples of compounds of Formula (I) are listed in Table 1.

TABLE 1

| Name | Structure | MW | Example |
|---|---|---|---|
| N-[2-(1,3-benzodioxole-5-yl)quinazolin-6-yl]acetamidine | 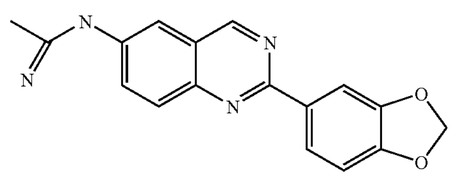 | 306.33 | 1 |
| N-[2-(1,3-benzodioxole-5-yl)quinolin-6-yl]acetamidine | 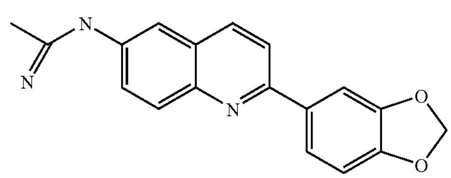 | 305.34 | 2 |
| N-[2-(2,3-dihydro-1,4-benzodioxin-6-yl)quinazolin-6-yl]acetamidine | 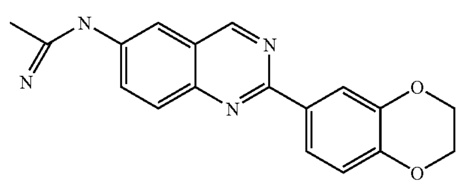 | 320.35 | 3 |
| N-[2-(2,3-dihydro-benzofuran-5-yl)quinazolin-6-yl]acetamidine | 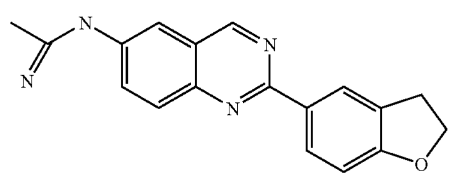 | 304.35 | 4 |
| N-[2-(benzofuran-5-yl)quinazolin-6-yl]acetamidine | 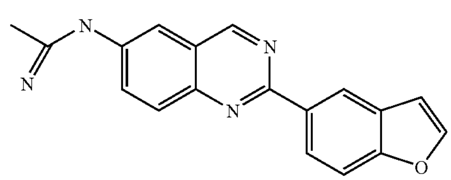 | 302.44 | 5 |

TABLE 1-continued

| Name | Structure | MW | Example |
|---|---|---|---|
| N-[2-(2,3-dihydro-benzo-furan-5-yl)quinolin-6-yl]acetamidine | | 303.37 | — |
| N-[2-(benzofuran-5-yl)quinolin-6-yl]acetamidine | 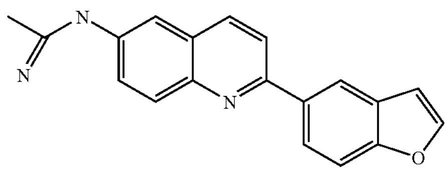 | 301.35 | — |
| N-[2-(benzofuran-6-yl)quinazolin-6-yl]acetamidine | 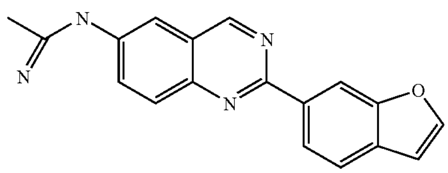 | 302.34 | — |
| N-[2-(2,3-dihydro-benzo-furan-6-yl)quinazolin-6-yl]acetamidine | | 304.35 | — |
| N-[2-(benzoxazol-5-yl)quinazolin-6-yl]acetamidine | 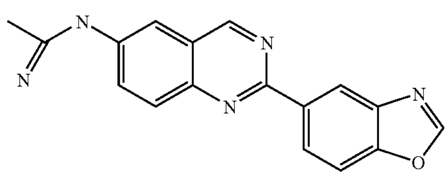 | 303.33 | — |
| N-[2-(benzimidazol-5-yl)quinazolin-6-yl]acetamidine | 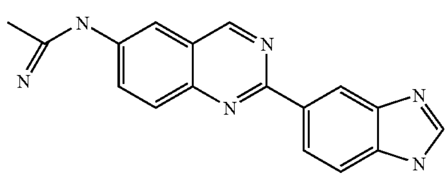 | 302.34 | — |
| N-[2-(benzoxazol-5-yl)quinolin-6-yl]acetamidine | 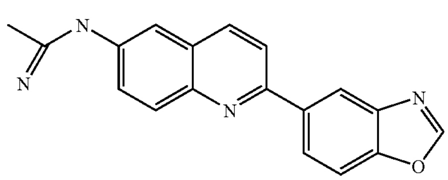 | 302.34 | — |
| N-[2-(benzimidazol-5-yl)quinolin-6-yl]acetamidine | 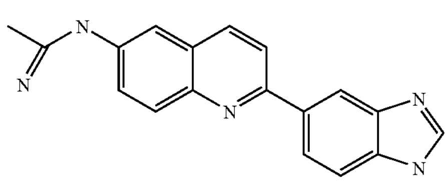 | 301.35 | — |
| N-[2-(1,4-benzodioxin-6-yl)quinazolin-6-yl]acetamidine | 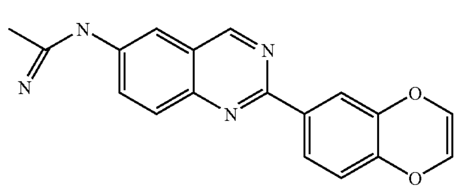 | 318.34 | — |

TABLE 1-continued

| Name | Structure | MW | Example |
|---|---|---|---|
| N-[2-(2H-3,4-dihydro-1-benzo-pyran-6-yl)quinolin-6-yl]acetamidine | 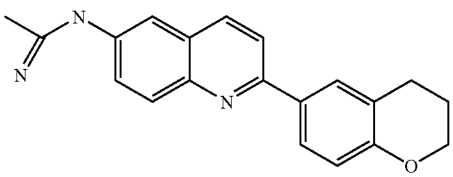 | 317.39 | — |
| N-[2-(2H-3,4-dihydro-1-benzo-pyran-6-yl)quinazolin-6-yl]acetamidine | 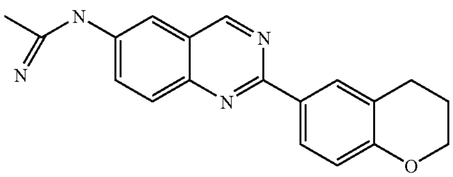 | 318.38 | — |
| N-[2-(2,4-dihydro-benzo-thiophen-1,1-dioxide-5-yl)quinazolin-6-yl]acetamidine | 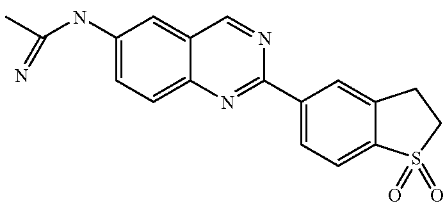 | 352.42 | — |
| N-[2-(1H-indol-5-yl)quina-zolin-6-yl]acetamidine | 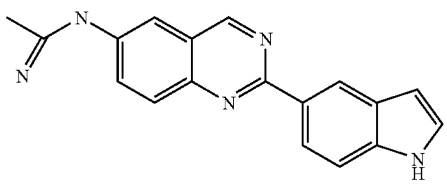 | 301.35 | — |
| N-[2-(2,4-dihydro-1H-indol-5-yl)quinazolin-6-yl]aceta-midine | 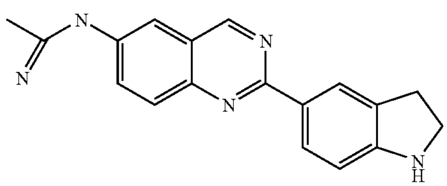 | 303.37 | — |

Preparation of the Compounds of the Invention

Compounds of Formula (I) are prepared by reacting a compound of Formula II with a compound of Formula (III) as depicted in Scheme 1, wherein X, Y, Z, Q, $R_1$ and $R_2$ have the same meanings as discussed above for compounds of Formula (I) while W is an alkoxy group (ethoxy or methoxy) or an alkylthio group (thiomethyl or 2-naphtylthiomethyl):

Scheme 1:

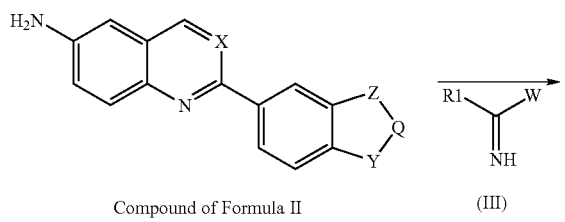

Compound of Formula II          (III)

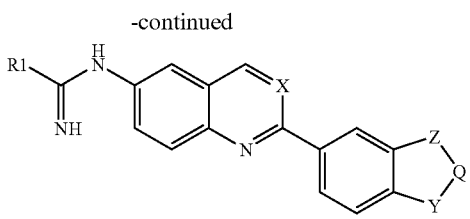

Compound of Formula I

The reaction of a compound of Formula (II) with a compound of Formula (III) is performed in a suitable solvent, such as: ethanol or methanol, acetonitrile, N,N-dimethylformamide (DMF) or tetrahydrofuran (THF), at a temperature between 0° C. and reflux temperature, analogously to the described procedures for alkoxyimidates (J. Med. Chem., 1990, 33, 2108-2113) or thioimidates (Tetrahedron Letters 1997, 179-182). Alternatively compounds of Formula (I) can be obtained from compounds of Formula (II) by reaction with the appropriate nitrile ($R_1$—CN), under dry hydrochloric acid catalysis; in the case of acetonitrile the nitrile itself can be the reaction solvent, for other cases a suitable inert solvent such as dichloromethane or tetrahydrofurane is used.

Optionally, the following steps can complete the conversion of a compound of Formula (II) into a compound of Formula (I):

removal of any protecting group present conversion of the product into a pharmaceutically acceptable salt or solvate.

Especially for those cases where in compounds of Formula (I) the Z-Q-Y substitution pattern is forming an heterocycle containing a basic nitrogen (typical examples being: 2,3-dihydroindole, 2,3-dihydro-[1,4]-benzothiazine, 2,3-dihydro-[1,4]-benzothiazine S,S-dioxide, 2,3-dihydro-[1,4]-benzoxazine) protection of this nitrogen is necessary before preparation of compounds of Formula (I). Suitable nitrogen protecting groups are in this case trifluoroacetamide, tert-butoxycarbonyl and benzyloxycarbonyl groups, more preferably the benzyloxycarbonyl protecting group. For these cases the protecting group removal will be the last step in the preparation of compounds of Formula (I). Conversion of a compound of Formula (I) into one of the above mentioned pharmaceutically acceptable salts or solvates or hydrates thereof, is easily achievable according to methods well known in the art. For example the acid addition salt or its solvate may be obtained by treatment of a compound of Formula (I) with an appropriate acid, in an inert solvent followed by precipitation, isolation and optionally re-crystallization by known methods.

Compounds of Formula (II) are obtained from compounds of Formula (III), as reported in Scheme 2, wherein X, Y, Z, Q, $R_1$, have the same meanings as discussed above for compounds of Formula (I). The nitro group reduction can be carried out by method well known in the art (P. Rylander, Catalytic Hydrogenation in Organic Synthesis, Academic Press, 1979), for example using hydrogen and a catalyst such as Pd/C or $PtO_2$, in a suitable solvent; alternatively the nitro group can be reduced using chemical reducing agents, such as stannous chloride (Bellamy, Tetrahedron Letters, 1984, 839-842) or iron (Merlic, JOC, 1995, 33-65).

Scheme 2:

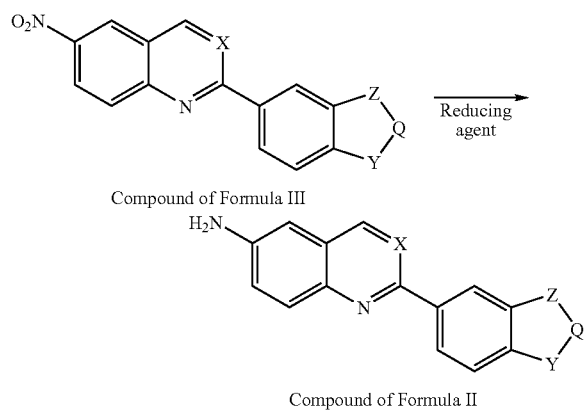

Compound of Formula III

Compound of Formula II

Alternatively a compound of Formula (II) can be obtained from a compound of Formula (IIIa), as reported in Scheme 3, wherein X, Y, Z, Q, have the same meanings as discussed above for compounds of Formula (I) and T is selected from the groups: $PhCH_2O$— or t But-O—, $CF_3$—, $CH_3$—, Ph-.

Scheme 3:

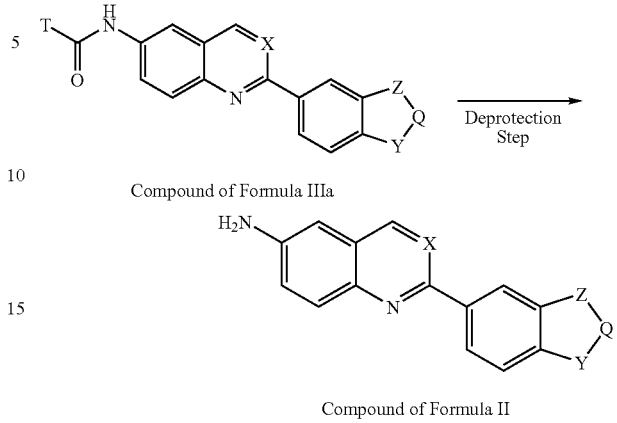

Compound of Formula IIIa

Compound of Formula II

The suitable conditions for protecting group removal will depend upon the used protecting group, and by the other protecting groups which could be present in the molecule, according to methods well known in the art (T. W. Green. and P. Wuts, Protective Groups in Organic Synthesis, 1991, J. W. & S.). For example, in the case the Z-Q-Y substitution pattern is forming an heterocycle containing a basic nitrogen (typical examples being: 2,3-dihydroindole, 2,3-dihydro-[1,4]-benzothiazine, 2,3-dihydro-[1,4]-benzothiazine S,S-dioxide, 2,3-dihydro-[1,4]-benzoxazine) protection of the nitrogen on the heterocycle is preferably achieved using a benzyloxycarbonyl group or a tert-butoxy carbonyl group while the T group will be preferably a —$CF_3$ or $CH_3$ group.

Compounds of Formula (III) and (IIIa) can be prepared by reacting compounds of Formula (IV) and (IVa) with compounds of Formula (V) in the case compounds Formula (III) and (IIIa) are quinolines derivatives, as detailed in Scheme 4:

Scheme 4:

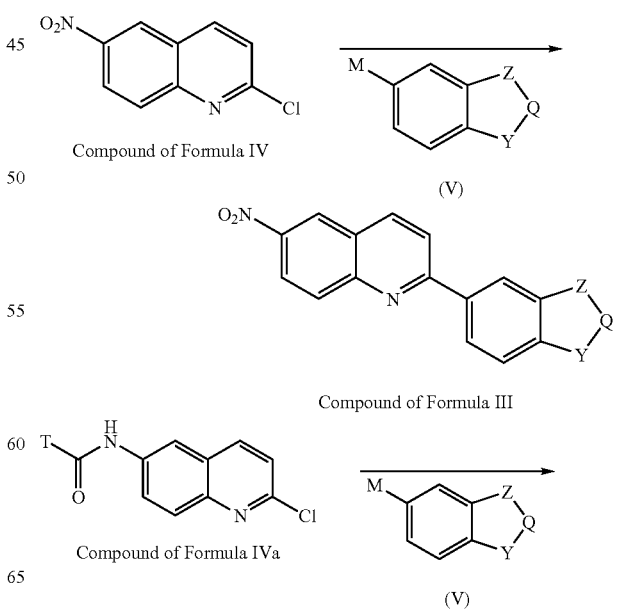

Compound of Formula IV (V)

Compound of Formula III

Compound of Formula IVa (V)

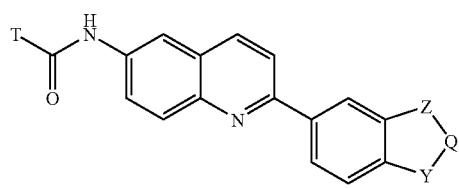

Compound of Formula IIIa

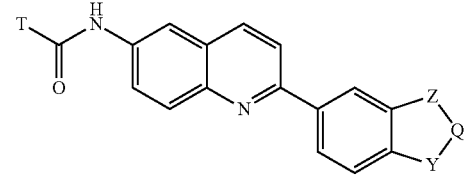

Compound of Formula IIIa

In Scheme 4, Y, Z, Q, have the same meanings as discussed above for compounds of Formula (I), T is as discussed above, and the substituent in position 2 of the quinoline derivative of Formula (IV) and (IVa) is a chlorine atom. In compounds of Formula (V) the substituent M is a metal containing group such as: boronate [—B(OH)$_2$], stannane [—Sn(Me)$_3$ or —Sn(nBut)$_3$], zinc (—ZnCl). When the M group is a boronate group the coupling reaction between a compound of Formula (IV) and a compound of Formula (V) can be carried out using the Suzuki diaryl-coupling, well known in the art (D. G. Hall, Boronic acids, Wiley-VCH, 2005). When the M group is a stannane, the coupling reaction can be carried out using the Stille's reaction (analogously to JOC, 2000, 2802-2805 or Bull. Chem. Soc. Jpn. 1983, 3855). When the M group is zinc (—ZnCl) the coupling reaction can be obtained using the known arylzinc diaryl-coupling procedure (analogously to JOC, 1997, 3158). Compounds of Formula (V) are commercially available or can be obtained from commercially available compounds by standard procedures. Compound of Formula (IV) and (IVa) are prepared as described by literature (Byoung, Heterocycles, 1998, 48, 12, 65).

Compounds of Formula (III) and (IIIa), in the case they are quinazoline derivatives, can be prepared by reacting compounds of Formula (VI) and (VIa) with compounds of Formula (VII), as detailed in Scheme 5.

Scheme 5

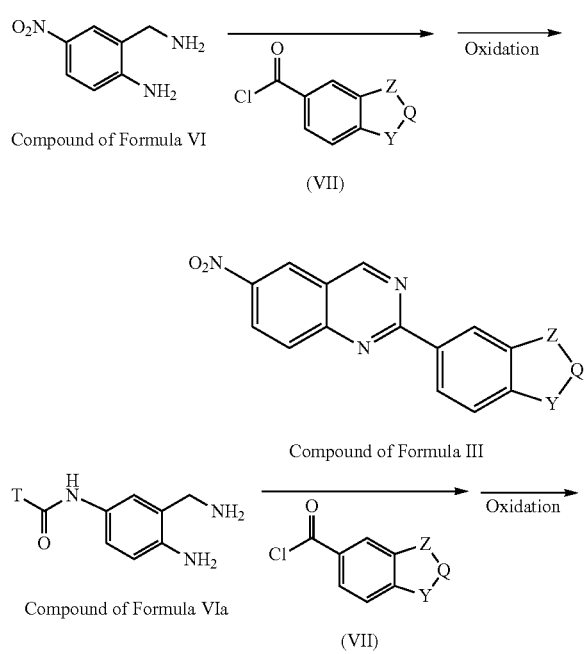

Reaction of compounds of Formula (VI) and (VIa) with acyl chlorides of Formula (VII) can be performed in the presence of an organic (for example triethylamine) or an inorganic (for example K$_2$CO$_3$) base, in a suitable inert solvent such as dichloromethane, dimethylformamide, dioxane, tetrahydrofurane and toluene, to provide the corresponding amides, that can be isolated or directly cyclized to the corresponding 3,4-dihydroquinazoline. Cyclization can occur spontaneously in the acylation medium or by heating the amides in the presence of an acid catalyst (such as para-toluensolfonic acid), in a suitable solvent (i.e. toluene), or by reaction of the amides with POCl$_3$ in an inert solvent such as toluene or dimethoxyethane. Oxidation of the intermediate 3,4-dihydroquinazoline to the corresponding compound of Formula (III) and (IIIa) can be obtained spontaneously by air oxidation or using oxidizing agents such as DDQ (2,3-dichloro-5,6-dicyanoquinone), TCQ (tetracyanoquinone) or MnO$_2$ depending upon the substrate. Compounds of Formula (VI) can be obtained from commercially available 5-nitro-anthranilonitrile, by reduction of the nitrile group with a suitable reducing agent such as borane in tetrahydrofurane, sodiumborohydride and nickel chloride or cobaltum chloride in methanol or ethanol, sodiumborohydride and borotrifluoride in ethyl ether or tetrahydrofurane. Compounds of Formula (VIa) can be prepared from commercially available 5-nitro-anthranilonitrile by protection of the 2-aniline group, reduction of the 5-nitro group, protection of the 5-anilino group, followed by deblocking of the 2-amino protecting group. The protecting groups should be suitably selected, for instance a trifluoroacetamido group can be introduced firstly onto the 2-amino group, then after reduction of the nitro group, the "orthogonal" tert-butoxycarbonyl protecting group can be introduced on the 5-amino group. Treatment with potassium carbonate in methanol will give rise to the selective removal of the trifluoroacetamido group. Alternatively, quinazolines of Formula (III) can be prepared by reacting the compound of Formula (VIII) with compounds of Formula (IX), as described in Scheme 6.

Scheme 6:

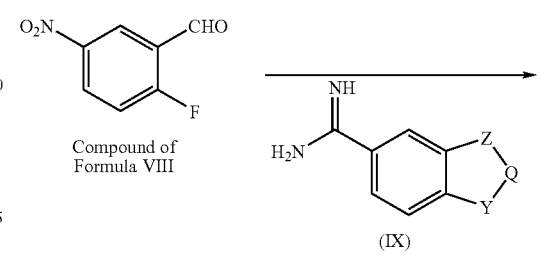

-continued

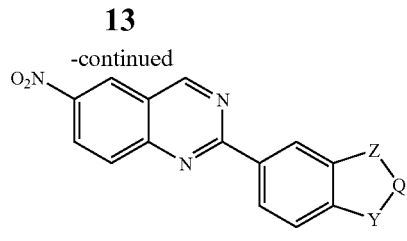

Compound of Formula III

The coupling reaction can be obtained according to standard methods, as reported by literature for analogous substrates (Woohdge, J. Med. Chem., 1975, 1117; Kotsuki Synlett, 1999, 1993). The compound of formula (VIII) is commercially available, compounds of formula (IX) can be prepared from commercially available compounds according to standard procedures.

Alternatively, quinazolines of Formula (II) can be prepared by reduction of tosylhydrazones of Formula (X) which are in turn obtained by 4-chloro-6-nitro-quinazoline of Formula (XI), as described in Scheme 7.

Scheme 7:

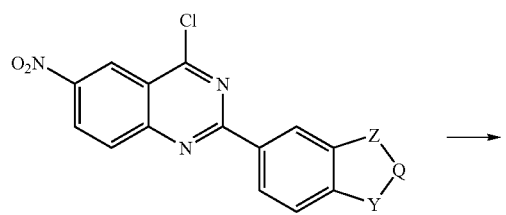

Compound of Formula XI

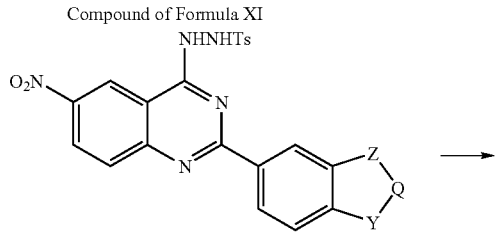

Compound of Formula X

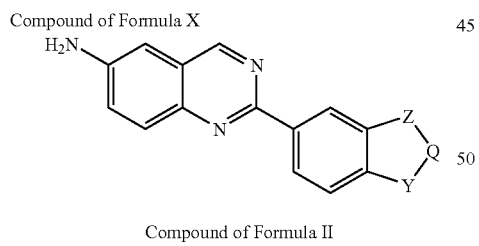

Compound of Formula II

Conversion of a compound of Formula (X) into a compound of Formula (II) can be obtained by using reducing agents such as hydrogen and Pd/C in a suitable solvent such as THF and ethanol in the presence of sodiumhydroxide, according to standard procedures, for example as described for analogous substrates (Gomtsyan, J. Med. Chem., 2005, 744). Compounds of Formula (XI) can be obtained by treatment of corresponding quinazolinones (XII) with SOCl$_2$, or POCl$_3$ or PCl$_3$. Quinazolinones of Formula (XII), as described in Scheme 8, are in turn obtained from bis-amides of Formula (XIII), by treatment with potassium hydroxide according to standard procedures.

Scheme 8:

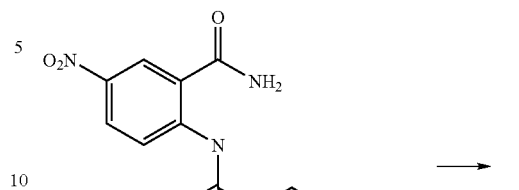

Compound of Formula XIII

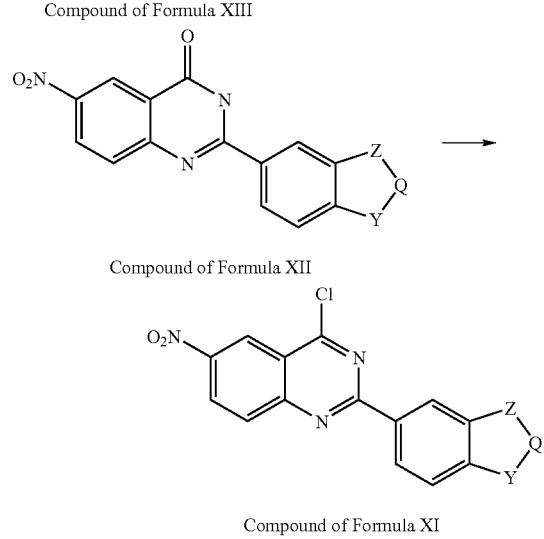

Compound of Formula XII

Compound of Formula XI

Amides of Formula (XIII) are obtained by hydrogen peroxide oxidation in aqueous sodium hydroxide of amido-nitriles of Formula (XIV), which are in turn obtained by reaction of 5-nitro-anthranilonitrile with the appropriate acyl-chloride of Formula (VII) as detailed in Scheme 9.

Scheme 9:

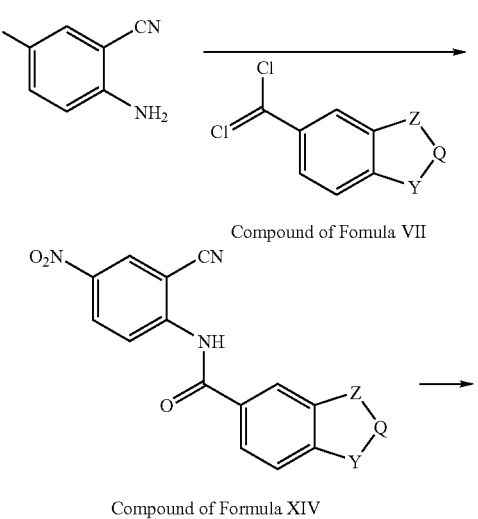

Compound of Formula XIV

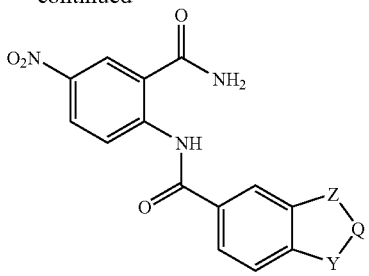

Compound of Formula XIII

Not limiting representative examples for preparations of compounds of Formula (I) are reported below.

Example 1

N-[2-(1,3-benzodioxol-5-yl)quinazolin-6-yl]acetamidine

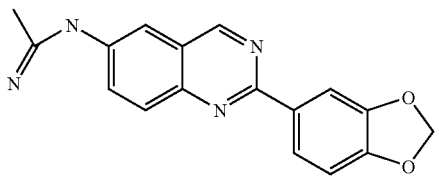

A suspension in ethanol (80 ml) of 6-amino-2-(3,4-methylendi-oxy-phenyl)-quinazoline (5 g, 0.019 mol) and S-2-naphthylmethyl thioacetimidate bromidrate (5.63 g, 0.019 mol, prepared as described in Tetrahedron Letters 38, 179-182 (1997), was stirred at r.t. for 24 hrs. Then S-2-naphthylmethyl thioacetimidate bromidrate (2.8 g, 0.010 mol) was added and the mixture was stirred at r.t. for further 24 hrs., then was concentrated under reduced pressure. The residue was partitioned between ethyl acetate and water. The aqueous layer was basified with $Na_2CO_3$ and extracted with ethyl acetate. The product was extracted with aqueous HCl (0.001 N) for three times. The aqueous layers were collected, basified with $Na_2CO_3$ and extracted with ethyl acetate. The organic layer was washed with water and dried over $Na_2SO_4$, concentrated under reduced pressure, and then the residue was triturated with diethyl ether. The yellow solid was filtered and dried in vacuum to give the titled product (2.4 g, 42% yield).

$C_{17}H_{14}N_4O_2$; MW: 306.33; mp 195.9-196.9° C.; $^1H$ NMR (DMSO-d6) 9.42 (s, 1H), 8.13 (d, 1H), 7.97 (s, 1H), 7.87 (d, 1H), 7.44 (s, 1H), 7.26 (s, 1H), 7.07 (d, 1H), 6.46 (s, 2H), 6.12 (s, 2H), 1.82-1.99 (m, 3H); IR (KBr) 3414, 1640, 1444, 1253; TLC ($CHCl_3:MeOH:H_2O:NH_3$ 85:25:2:1) Rf=0.65

6-amino-2-(1,3-benzodioxol-5-yl)-quinazoline

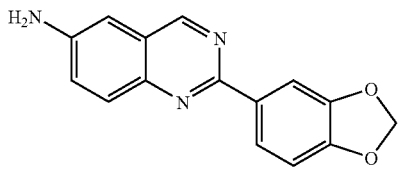

A suspension of 6-nitro-2-(1,3-benzodioxole-5-yl)-quinazoline (37 g, 0.126 mol) and $SnCl_2$ $2H_2O$ (117.2 g, 0.504 mol) in ethanol (500 ml) was heated at reflux for 1 h. After cooling to r.t., the solvent was removed under reduced pressure, chloroform was added and the mixture was basified with ammonia. The precipitate was filtered off and washed with chloroform. The filtrates were collected, washed with water and then dried over $Na_2SO_4$. The solution was concentrated under reduced pressure, and then the residue was triturated with diisopropyl ether/petroleum ether. The yellow solid was filtered and dried in vacuum (21.2 g, 64% yield).

$C_{15}H_{11}N_3O_2$, MW: 265.27; mp 191-192° C.; $^1H$ NMR (DMSO-d6) 9.24 (s, 1H), 8.05 (dd, 1H), 7.91 (d, 1H), 7.73 (d, 1H), 7.39 (dd, 1H), 7.03 (d, 1H), 6.90 (d, 1H), 6.11 (s, 2H), 5.93 (s, 2H); IR (KBr) 3319, 3203, 1631, 1500, 1446; TLC (CHCl3/MeOH 9/1) Rf=0.3.

6-nitro-2-(1,3-benzodioxol-5-yl)-quinazoline

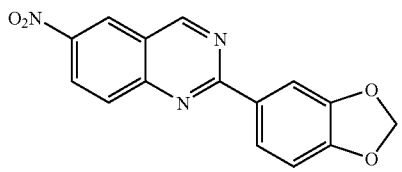

To a suspension of 5-nitro-2-amino-benzylamine hydrochloride (31 g, 0.152 mol) in dichloromethane (DCM) (450 ml) was added at 0° C. TEA (52.6 ml, 0.38 mol) and a solution of piperonyloyl chloride (27.3 g, 0.16 mol) in DCM (80 ml). The mixture was stirred for 2 hours at r.t. The solvent was removed under reduced pressure and the residue was triturated with ethanol/water 1/9 and then with diisopropyl ether. The obtained solid was dried in vacuum and suspended in toluene (900 ml) and $POCl_3$ (670 ml). The mixture was heated at reflux for 2 hours and after the removal of solvent the residue was triturated with water/ammonia, washed with water and dried over $P_2O_5$. A mixture of the obtained solid and chloranile (32.7 g, 0.129 mol) in toluene (500 ml) was heated at reflux for 2 hours. The mixture was concentrated under reduced pressure and the residue was triturated with NaOH 1M, washed with water and with methanol. The obtained solid was dried in vacuum (37 g, 83% yield). $C_{15}H_9N_3O_4$, MW=295.26. mp: 220-222° C.

5-nitro-2-amino-benzylamine hydrochloride

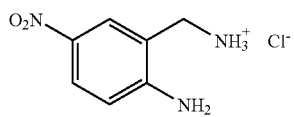

A solution of borane in THF (1 M, 840 ml) was added to a suspension of 5-nitro-anthranilonitrile (120 g, 0.70 mol) in THF (1.2 L) under nitrogen at 0° C. The mixture was stirred for 2 hours at r.t. After cooling at 0° C. EtOH absolute (400 ml) was added, then HCl was bubbled for 45 minutes. The mixture was concentrated under reduced pressure and the residue was triturated with ethanol and then with diisopropyl ether. The obtained solid was dried in vacuum to give the hydrochloride salt (140 g, 99% yield). C₇H₁₀N₃O₂Cl, MW: 203.63. TLC (CHCl₃:MeOH:H₂O:NH₃ 85:25:2:1) Rf=0.3.

Example 2

N-[2-(1,3-benzodioxol-5-yl)quinolin-6-yl]acetamidine dihydrochloride

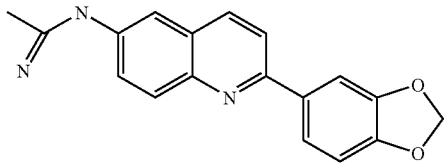

6-amino-2-(1,3-benzodioxol-5-yl)-quinoline (1.0 g, 3.78 mmol) is dissolved in acetonitrile (30 ml). The solution is cooled to 0° C. and HCl$_{(gas)}$ is bubbled for 30 minutes. The reaction mixture is stirred at r.t. for 12 hours. The product is filtered off and washed with acetonitrile and isopropyl ether. 1.5 g of yellow solid was obtained.

C₁₈H₁₇Cl₂N₃O₂, M.W.: 378.26; m.p: 261.4-265.5° C.; ¹H-NMR (d₆-DMSO): 11.93 (s, 1H); 9.75 (s, 1H); 8.80 (s, 1H); 8.57 (d, 1H); 8.27-8.23 (m, 2H); 8.03 (s, 1H); 7.91 (d, 2H); 7.88 (d, 1H); 7.12 (d, 1H); 6.16 (s, 2H); 5.90 (m, 1H). IR(KBr): 3394, 2772, 1598, 1501, 1345, 1259 cm⁻¹.

Rf (85/25/2/1 chloroform/methanol/ammonia/water): 0.65; HPLC: retention time 8.46 minutes HPLC conditions: Supelcosil LC-DP column; 150×46 mm; eluent KH₂PO₄ 10 mM with 25/27/48 H₃PO₄/methanol/acetonitrile (pH=3.7); flow 0.45 ml/min; UV detector at 214.0 nm.

6-amino-2-(1,3-benzodioxol-5-yl)-quinoline

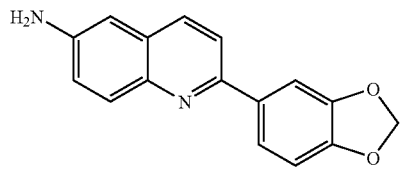

10% Pd/C (0.29 g, 0.27 mmol) is added to 2-(1,3-benzodioxol-5-yl)-6-nitroquinoline (2.0 g, 6.80 mmol) in methanol/THF (80 ml/80 ml). The mixture is hydrogenated at r.t. for 2 hours. The catalyst is filtered off and the filtrate is concentrated to afford 1.31 g (73%) of the titled product.

C₁₆H₁₂N₂O₂, M.W. : 264.29. ¹H-NMR (d₆-DMSO): 8.00 (d, 1H); 7.83-7.63 (m, 4H); 7.20 (d, 1H); 7.16 (d, 1H); 6.84 (s, 1H); 6.07 (s, 2H); 5.65 (s, 2H). Rf (9/1 chloroform/methanol): 0.50.

2-(1,3-benzodioxol-5-yl)-6-nitroquinoline

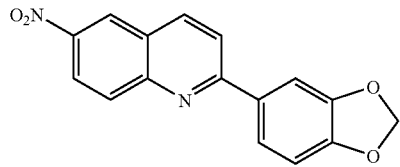

2-chloro-6-nitroquinoline (5.2 g, 25 mmol) (prepared according to Byoung S. L. et al. Heterocycles. 1998, 48.12, 65), 3,4-(methylenedioxy)phenylboronic acid (5.0 g, 30 mmol), palladium dichloride bis(triphenilphosphine) (350 mg, 0.5 mmol) and barium hydroxide octahydrate (18.9 g, 60 mmol) in 150 ml of anhydrous THF are stirred at 65° C. for 20 hours. The mixture of reaction is evaporated under vacuum and the residue is chromatographed on silica gel (CH₂Cl₂) to afford 2.0 g (27%) of the titled product.

C₁₆H₁₀N₂O₄, M.W: 294.27, ¹H-NMR (d₆-DMSO): 8.95 (s, 1H); 8.65 (s, 1H); 8.95 (d, 1H); 8.40 (dd, 1H); 8.19-8.11 (m, 2H); 7.87 (d, 2H); 7.05 (d, 1H); 6.10 (s, 2H). Rf(CH₂Cl₂): 0.50.

Example 3

N-[2-(2,3-dihydro-1,4-benzodioxin-6-yl)quinazolin-6-yl]acetamidine

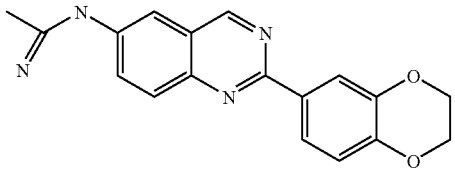

This compound was synthesized in 46% yield, according to the procedure described in example 1 for the synthesis of N-[2-(1,3-benzodioxole-5-yl)quinazolin-6-yl]acetamidine.

C₁₈H₁₆N₄O₂, MW: 320.35, mp 191.7-192.6° C.; ¹H NMR (DMSO-d₆) 9.42 (s, 1H), 7.98-8.05 (m, 2H), 7.87 (d, 1H), 7.20-7.46 (m, 2H), 7.00 (d, 1H), 6.40 (s, 1H), 4.33 (s, 4H), 1.70-2.10 (m, 3H); IR (KBr) 3439, 1638, 1558, 1432, 1347; TLC(CHCl₃:MeOH:H₂O:NH₃ 85:25:2:1) Rf=0.38.

6-amino-2-(2,3-dihydro-1,4-benzodioxine-6-yl)-quinazoline

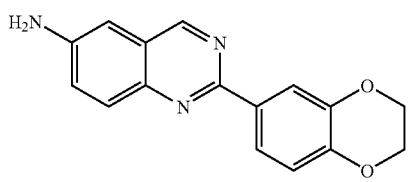

This compound was synthesized in 67% yield, according to the procedure described in example 1 for the synthesis of 6-amino-2-(1,3-benzodioxol-5-yl)-quinazoline.

C₁₆H₁₃N₃O₂, MW: 279.30, mp 179.4-181.6° C.; ¹H NMR (DMSO-d6) 9.24 (s, 1H), 7.92-7.98 (m, 2H), 7.72 (d, 1H), 7.38 (dd, 1H), 6.89-6.99 (m, 2H), 5.91 (s, 2H), 4.31 (s, 4H); IR (KBr) 1555, 1507, 1286; TLC (CHCl$_3$/MeOH/NH$_3$ 95/5/0.5) Rf=0.50.

6-nitro-2-(2,3-dihydro-1,4-benzodioxine-6-yl)-quinazoline

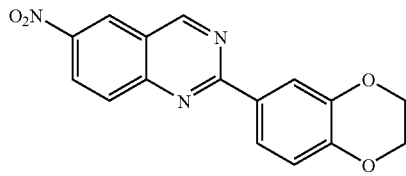

This compound was synthesized in 70% yield, according to the procedure described in example 1 for the synthesis of 6-nitro-2-(1,3-benzodioxole-5-yl)-quinazoline.
C$_{16}$H$_{11}$N$_3$O$_4$, MW: 309.28. mp. 263-265° C.; TLC (tol/AcOEt 7/3) Rf=0.80.

Example 4

N-[2-(2,3-dihydro-benzofuran-5-yl)quinazolin-6-yl] acetamidine dihydrochloride hemihydrate

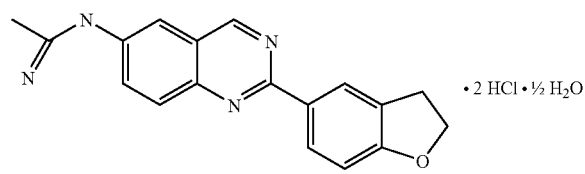

A suspension of 6-amino-2-(2,3-dihydro-5-benzofuryl)-quinazoline (1.4 g, 0.0053 mol) in MeCN (50 ml) was satured with HCl at 0° C. and stirred at r.t. for 24 hrs. The precipitated was filtered and triturated with acetone/methanol. The light yellow solid was filtered and dried in vacuum at 40° C. to give the titled compound, 1.3 g, 65% yield).
C$_{18}$H$_{18}$N$_4$OCl$_2$, MW: 377.27. mp 186-192° C. $^1$H NMR (DMSO-d6) 11.93 (s, 1H), 9.80 (s, 1H), 9.70 (s, 1H), 8.84 (s, 1H), 8.38-8.46 (m, 2H), 8.10-8.15 (m, 2H), 7.89 (dd, 1H), 6.95 (d, 1H), 4.66 (t, 2H), 3.32 (t, 2H), 2.44 (s, 3H); IR (KBr) 3037, 1611, 1505, 1243; TLC(CHCl$_3$:MeOH:H$_2$O:NH$_3$ 85:25:2:1) Rf=0.58.

6-amino-2-(2,3-dihydro-benzofuran-5-yl)-quinazoline

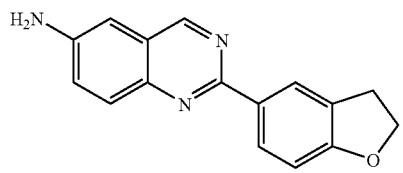

This compound was synthesized in 73% yield, according to the procedure described in example 1 for the synthesis of 6-amino-2-(1,3-benzodioxol-5-yl)-quinazoline.
C$_{16}$H$_{13}$N$_3$O, MW: 263.30. TLC(CHCl3/MeOH 9/1) Rf=0.65.

6-nitro-2-(2,3-dihydro-benzofuran-5-yl)-quinazoline

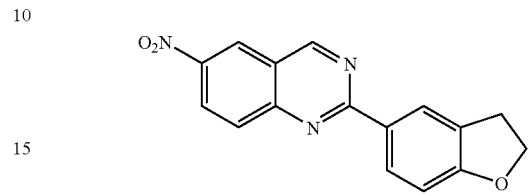

This compound was synthesized in 15% yield, according to the procedure described in example 1 for the synthesis of 6-nitro-2-(1,3-benzodioxol-5-yl)-quinazoline.
C16H$_{11}$N$_3$O$_3$, MW: 293.28. $^1$H NMR (DMSO-d6) 9.91 (s, 1H), 9.17 (d, 1H), 8.66 (dd, 1H), 8.42-8.49 (m, 2H), 8.15 (d, 1H), 6.97 (d, 1H), 4.68 (t, 2H), 3.28 (t, 2H).

Example 5

N-[2-(2,3-dihydro-benzofuran-5-yl)quinazolin-6-yl] acetamidine dihydrochloride

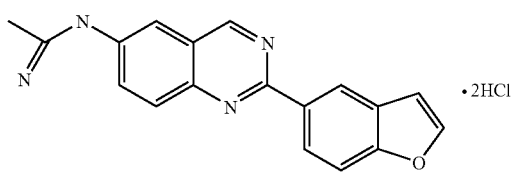

This compound was synthesized in 19% yield, according to the procedure described in example 1 for N-[2-(1,3-benzodioxolyl)quinazoline-6-yl]acetamidine. The free base was converted into the hydrochloride salt by treating its methanol suspension with isopropyl ether/HCl and evaporating the resulting suspension. The solid was triturated in acetone and dried under vacuum at 40° C.
mp 190-195° C.; $^1$H NMR (DMSO-d6) 12.10 (s, 1H), 9.89 (s, 1H), 9.79 (s, 1H), 8.92 (d, 1H), 8.60 (dd, 1H), 8.11-8.22 (m, 3H), 7.94 (d, 1H), 7.79 (d, 1H), 7.16 (d, 1H), 5.26 (s, 2H), 2.47 (s, 3H); IR (KBr) 2802, 1678, 1610, 1503; TLC (CHCl$_3$/MeOH/H$_2$O/NH$_3$ 85/25/2/1) Rf=0.28.

6-amino-2-(5-benzofuran)-quinazoline

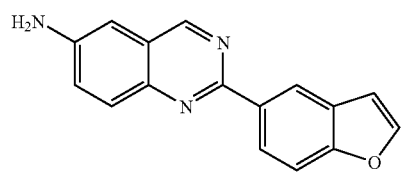

This compound was synthesized in 59% yield, according to the procedure described in example 1 for the synthesis of 6-amino-2-(1,3-benzodioxol-5-yl)-quinazoline.

¹H NMR (DMSO-d6) 9.31 (s, 1H), 8.77 (s, 1H), 8.48 (dd, 1H), 8.06 (d, 1H), 7.68-7.80 (m, 2H), 7.41 (dd, 1H), 7.10 (d, 1H), 6.93 (d, 1H); TLC (tol/AcOEt 7/3) Rf=0.35

Synthesis of 6-nitro-2-(5-benzofuran)-quinazoline

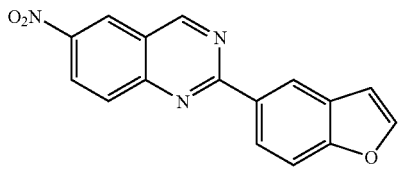

This compound was synthesized in 76% yield, according to the procedure described in example 1 for the synthesis of 6-nitro-2-(1,3-benzodioxol-5-yl)-quinazoline. TLC (tol/AcOEt 7/3) Rf=0.80

Pharmacological Evaluation of the Compounds of the Invention

The efficacy of the compounds of Formula (I) for the treatment of inflammatory or neuropathic pain along with the inflammatory related disorders mentioned above has been determined using the following in vitro assays and in vivo animal models.

Compounds of the invention are not effective in inhibiting cycloxygenase enzymes (COX-1 and COX-2), since they have been proved not to be effective up to $10^{-5}$ M concentration, in standard in vitro test either for COX-1 or for COX-2 enzyme inhibition.

Conversely, compounds of the invention are able to inhibit, at micromolar concentration, IL-1β induced $PGE_2$ production in cellular systems. This inhibition effect on the production of the pro-inflammatory mediator $PGE_2$, instead of to be ascribed to a direct COX-2 inhibition, as happens with Celecoxib and other COX-2 inhibitors, is in this case due to inhibition of cytokine induced COX-2 expression as proven in cellular systems.

Effectiveness in inhibition of $PGE_2$ production induced by IL-1β in chondrocyte cell culture, as well as inhibition in IL-1β induced COX-2 expression in SW1353 human chondrosarcoma cell line, is summarized in Table 2, for representative compounds of the invention.

TABLE 2

| Compound | Effects on $PGE_2$ production in rabbit Chondrocyte culture | Inhibition of COX-2 expression in SW1353 human chondrosarcoma cell line |
|---|---|---|
| Example 1 | $IC_{50}$ = 4.1 µM | $IC_{50}$ = 4.6 ± 1.2 µM |
| Example 2 | 70% at 10 µM | 59% at 10 µM |

Furthermore compounds of the invention are not effective in inhibiting nitric oxide synthase enzymes, since they have been proved not to be effective even at the higher concentrations, in standard in vitro test for iNOS and nNOS enzyme inhibition. In addition no activity in inhibition of IL-1β induced NO production in cellular systems was found, as well as the compounds were found not effective in inhibiting iNOS expression in IL-1β stimulated SW1353 human chondrosarcoma cell line.

The compounds of the invention have been found effective in interfering with cytokine production in several cell lines, representative examples of this effect are reported in Table 3, for two representative cytokines, in IL-1 stimulated human chondrosarcoma cell line.

TABLE 3

| Compound | Inhibition (%) of IL-1 production | Inhibition (%) of IL-6 production |
|---|---|---|
| Example 1 | 50% | 65% |
| Example 2 | 45% | 78% |

Compound concentration is 10 µM.

To this cytokine modulator property can be ascribed completely or in part the striking anti-inflammatory and analgesic properties displayed by the compounds of the invention in in vivo models of inflammation and pain (M. Schafer, Cytokines and Peripheral Analgesia, Immune Mechanisms of Pain and Analgesia, pg. 41-50 Plenum Publishers, 2003).

The interplantar injection of Zymosan-induced mechanical hyperalgesia was used as a model of inflammatory pain (Meller, Neuropharmacology, 1994, 33, 1471-1478). In this model, typically a male Sprague-Dawley or Wistar rat (200-250 g) receives an interplantar injection of 3 mg/100 µl zymosan into one hind paw. A marked inflammation occurs in this hind paw. Drugs are administered orally for evaluation of efficacy, 30 min. before the inflammatory insult. The hyperalgesia induced by zymosan administration was evaluated using the Randall-Selitto method (Arch. Int. Pharmacodyn., 1957, 111, 409). The quantitation of the analgesic effect is achieved by an analgesimeter, which consist in applying to the inflamed paw an increasing weight (from 130-140 g up to 500 g). The difference in the mechanical pain threshold between the basal value (generally 230-250 g) and the one tolerated by the animals treated with the drug, determined 4 hours after the inflammatory challenge, is defined as mechanical hyperalgesia.

Mechanical hyperalgesia is expressed for the compounds of the invention as $ED_{50}$, which is the dose of the administered compound able to increase the pain threshold by 50% in comparison with the group of control animals. The corresponding $ED_{100}$, representing the dose able of reducing of 100% the pain threshold, can be calculated for those cases where there is a linear dose-response relationship. In vivo anti-inflammatory effect exerted by the compound of the invention can be assessed in the same Zymosan induced inflammation test described above, by measuring the volume of the oedema induced by the inflammatory agent. The oedema was evaluated as the increase in the volume of the Zymosan injected paw within a time of 0-2 hrs. The measurements of the variation of the oedema volume of the paw were recorded using hydroplethysmometer, which consists of two plastic cuvettes containing a surfactant liquid, the larger one being used for immersion of the paw, connected to the smaller one which contains a trans-ducer capable of recording small displacements of the volume used for the measure. The paw is immersed in the cuvettes up to the tibiotarsal joint. The volume of the liquid displaced is proportional to the extent of the inflammation. The efficacy of the compounds of the invention in preventing oedema formation is expressed as $ED_{30}$, and is measured 2 hours after the inflammatory challenge, and represents the dose able of reducing of 30%, the Zymosan induced paw volume increase in comparison to control animals (animals treated with Zymosan but treated with only distilled water instead of the testing compound). The corresponding $ED_{50}$, representing the dose able of reducing of 50% the zymosan induced paw volume increase, can be calculated for those cases where there is a linear dose-response relationship.

In both the experiments, for each test compound, at least three doses were used, with 10 animals per group. Compounds of the invention were tested at 10, 20 and 40 mg/Kg.

The performance of representative compounds of Formula (I), in the tests described above, is summarized for both the analgesic effect and the anti-inflammatory effect in Table 4, where the activity of the compounds of the invention is compared by the performance in the same test of well known standards.

Representative compounds of the invention demonstrated efficacy superior or comparable to the standards both in a test of analgesia and for anti-inflammatory effects. In addition, compounds of the invention did not displayed ulcerative side effects comparable to the ones displayed by Nimesulide, even at the higher doses tested.

TABLE 4

| Compound | Analgesia (mg/kg) | | Oedema Reduction (mg/kg) | |
|---|---|---|---|---|
| | $ED_{50}$ | $ED_{100}$ | $ED_{30}$ | $ED_{50}$ |
| Example 1 | 6 | 18 | 12.2 | 23.1 |
| Example 2 | 10.7 | 22 | 15.0 | 98 |
| Example 4 | 5.8 | 17 | 25 | 170 |
| Celecoxib | 9 | 1172 | 13.8 | 644 |
| Tramadol | 25.7 | 405 | NE | NE |
| Nimesulide | 7.4 | 161 | 0.5 | 33.4 |

NE: not effective

Analgesic activity of the compounds of Formula (I) can be further evaluated in an animal model of chronic inflammatory pain. Since clinically, inflammatory pain is most often associated with chronic conditions such as arthritis and chronic lower back pain, where any inflammation or plastic neuronal change in the peripheral and central nervous system would have been occurring for long time, chronic animal paradigms in which the inflammatory insult has had time to induce centrally mediate changes, may result more predictive models. The original model of chronic inflammatory pain was based on injection of inflammatory mediator (adjuvant) into the base of the tail in rats. As a consequence of this treatment, a polyarthritis comprising profound inflammation and hyperalgesia initially at the site of the injection occurs. However, due to T-cell mediated hypersensivity reaction, the disease develops, in a couple of weeks, in multiple joint involvement and subsequent lesions to eyes, ears, nose and genitals. These global effects are not reflecting those clinically observed in common pathologies characterized by chronic inflammatory pain. More recently, it was shown how the use of Complete Freund's Adjuvant (CFA; *Mycobacterium tuberculosis*) as triggering agent for the inflammatory response along with the use of an appropriate protocol can give rise to a more suitable model. CFA-induced prolonged inflammation has been used extensively in studies of behavioural pain response (K. Walker, Animal Models for Pain Research, Mol Med Today, 1999, 5,319-321) since it has been considered also suitable for studying involvement of neuronal plasticity in chronic pain (S, Naeini, Remodelling of spinal nociceptive mechanisms in an animal model of monoarthritis, Eur. J. Neuroscience, 2005, 22, 8, 2005-2015).

Experiments are performed as described in the literature (C. J. Woolf, Cytokine, Nerve Growth Factor and Inflammatory Hyperalgesia: the Contribution of Tumor Necrosis Factor α, Br. J. of Pharmacology, 1997, 121, 417-424); 8 rats were used for each group, each product was tested at three doses (3, 10, 30 mg/kg), the products were administered i.p., 24 hours after the interplantar challenge, and the analgesic activity was measured starting from the 24 hours following the challenge. In Table 5, results obtained in the CFA model, for representative compounds of Formula (I) are listed in comparison to Piroxicam, a recognized standard. Analgesic effect is assessed using the same equipment as before described for the Randall-Selitto model, results are reported as maximum percent effect (MPE) which represents the difference (%) in pain threshold between the animals treated with the drug and the controls that received only the vehicle (reduction of the nociceptive effect, due to paw loading with increasing weight, in comparison to controls which received CFA treatment). 100% protection means that the animal treated with the compound and CFA can tolerate the same stimulus (weight) as the control animal which has not received CFA treatment. MPE higher than 100% mean that the animal treated with the compound and CFA can tolerate stimuli (weight) higher than the control animals, which has not received CFA treatment (hypoalgesia).

TABLE 5

| | CFA | | | | | |
|---|---|---|---|---|---|---|
| Compound | Dose mg/Kg | MPE 0.5 hrs. | MPE 1.5 hrs. | MPE 3 hrs. | MPE 6 hrs. | MPE 24 hrs. |
| Example 1 | 3 | 9 | NE | NE | NE | NE |
| | 10 | 28 | 47 | 15 | 30 | NE |
| | 30 | 418 | 395 | 384 | 132 | 60 |
| Example 2 | 3 | 36 | 40 | 7 | NE | NE |
| | 10 | 94 | 34 | 11 | NE | 13 |
| | 30 | 188 | 81 | 34 | NE | 9 |
| Example 4 | 3 | NE | 44 | NE | NE | NE |
| | 10 | 47 | 27 | 25 | 66 | 57 |
| | 30 | 243 | 270 | 170 | 103 | 76 |
| Piroxicam | 30 | 102 | 111 | 54 | 24 | 38 |

NE: Not Effective

The compounds of the invention demonstrated also in this test a pronounced, long lasting analgesic effect, at doses of 10 and 30 mg/Kg, being the highest dose characterized with a remarkable hypoalgesic effect. At this dose the representative compounds are much more effective than Piroxicam, the reference standard.

Painful diabetic neuropathy is one of the most common complications of insulin-dependent diabetes in man; in particular, diabetes can be associated with neuropathic pain which fails to be treated by classical analgesics.

Streptozotocin (STZ)-induced diabetes in the rat has been increasingly used as a model of painful diabetic neuropathy to assess the efficacies of potential analgesic agents (C. Courteix, Pain 1993, 53, 81-8). The compounds of the invention were tested for efficacy in reducing mechanical hyperalgesia associated with STZ-induced diabetes in the rat, according to the experimental model as described by the literature. Diabetes was produced with the injection of a single dose (75 mg/Kg i.p.) of STZ. In the following four weeks after the induction of diabetes the clinical symptoms (weight, body and skin temperature, motility and hyperglycemia) progressively developed by the animals, are strictly monitored. After four weeks, the scores obtained in diabetic rats to various pain stimuli (in particular mechanical stimuli) were grater than those in normal rats, indicating hyperalgesia. The hyperalgesia induced by diabetes was evaluated using the Randall-Selitto method as above described, and quantitated using the analgesimeter. Also in this case, the difference in the mechanical pain threshold between the basal value (generally 230-250 g) and the one tolerated by the animals treated with the drug, is defined as mechanical hyperalgesia. The compounds of the invention were administered i.p. (solution, Tween 80, 10% in saline) at different doses, and mechanical hyperalgesia was measured at the reported time, as maximum percent effect (MPE) which represents the difference (%) in pain threshold between the animals treated with the drug and the controls that received only the vehicle, compared with the weight borne by naïf non-diabetic controls. A 100% protection means that the diabetic animals treated with the compound can tolerate the same stimulus (weight) as the naïf non-diabetic animals. MPE higher than 100% means that the diabetic animal treated with the compound can tolerate stimuli (weight) higher than the control non-diabetic animals (hypoalgesia).

In Table 6, the performance of a representative compound of Formula (I), in the above described model of neuropathic pain, is compared with some known pharmacological standards used for the clinical treatment of this pathology.

TABLE 6

Neuropathic Pain

| Compound | Dose mg/Kg | MPE 0.5 hrs. | MPE 1.5 hrs. | MPE 3 hrs. |
| --- | --- | --- | --- | --- |
| Example 1 | 3 | 15 | 30 | 45 |
|  | 10 | 59 | 34 | 46 |
|  | 30 | 110 | 137 | 101 |
| Example 2 | 3 | 32 | 75 | 8 |
|  | 10 | 76 | 107 | 13 |
|  | 30 | 151 | 124 | 93 |
| Example 4 | 3 | 56 | 15 | NE |
|  | 10 | 78 | 24 | NE |
|  | 30 | 163 | 74 | NE |
| Gabapentin | 10 | NE | NE | NE |
|  | 30 | NE | NE | NE |
|  | 100 | NE | NE | NE |
|  | 300 | NE | NE | NE |
| Amitriptyline | 1 | 72 | 89 | NE |
|  | 3 | 44 | 40 | 5 |
|  | 10 | 68 | 77 | NE |
|  | 30 | 65 | 69 | 23 |
| Tramadol | 3 | 26 | 53 | 7 |
|  | 10 | 58 | 48 | 27 |
|  | 30 | 54 | 64 | 23 |
|  | 50 | 81 | 60 | 43 |

NE: not effective

Whereas the compounds of Examples 1, 2, and 4 demonstrated to be quite effective, especially at the doses of 30 mg/kg, (i.e. protection higher than 100%). All of the standards used exhibited a much lower efficacy, if any, in this paradigm.

With the aim of assessing whether the compounds of the invention are able to inhibit responses to peritoneal irritation-induced visceral pain, the acetic acid-induced writhing assay was used in mice to determine the degree of anti-nociception.

The writhing test is a model of inflammatory pain that has long been used as a screening tool for evaluation of analgesic and anti-inflammatory agents (HDJ Collier, B. J. Pharmacol Chemother., 1968, 32, 295-310). The test was performed inducing nociception by an i.p. injection of acetic acid 1%, 0.1 mL/10 g of body weight. Mice were pre-treated (subcutaneously, s.c., three different doses: 3, 10, 30 mg/Kg) with the tested compounds 30 min. before acetic acid injection, while control animals received a similar volume of saline solution. A group of mice was treated with Paracetamol (200 mg/Kg, s.c.) as reference drug. The number of abdominal writhes (full extension of both hind paws) was cumulatively counted every 5 minutes over a period of 20 min. immediately after the acetic acid injection. The anti-nociceptive activity was expressed as inhibition of abdominal writhes as maximum percent effect (MPE), which represents the difference (%) in pain threshold between the animals treated with the drug and the ones that received only the vehicle.

In order to assess the possible not specific sedative or motor effects of the investigated compounds, and to distinguish analgesia from drug-induced motor changes, the motor activity of the animals that received the tested compounds was compared to mice receiving only the vehicle.

In Table 7, the performance of representative compounds of Formula (I), in the above described test of analgesia and peritoneal irritation-induced visceral pain, are compared with Paracetamol.

TABLE 7

Writhing test:

| Compound | Dose mg/Kg | MPE (%) | $ED_{50}$ (mg/Kg) |
| --- | --- | --- | --- |
| Example 1 | 3 | 30 | 9.8 |
|  | 10 | 33 |  |
|  | 30 | 89 |  |
| Example 2 | 3 | 59 | <3.0 |
|  | 10 | 61 |  |
|  | 30 | 57 |  |
| Example 4 | 3 | 18 | 59.6 |
|  | 10 | 41 |  |
|  | 30 | 36 |  |
| Paracetamol | 200 | 61 | — |

Compounds of the invention where found much more effective than the standard in inhibiting peritoneal irritation-induced visceral pain. None of the tested compounds induced significant motor changes, indicating that they give analgesia devoid of non specific sedative or stimulating effects.

The formalin test is increasingly used as a model of injury-produced pain (FV. Abbott, Pain, 1995, 60, 91-102). The procedure used for the evaluation of the compounds of the invention was similar to that reported by literature (S. Hunskaar, Pain, 1987, 30, 103-104), and consisted of the injection of 20 µl of 1% solution of formalin dissolved in distilled water, in the plantar surface of the right hind paw of the mice. Immediately, the animals were placed individually in an observation chamber. The amount of time that the animal spent licking the injected paw, considered indicative of pain, was recorded during 30 min. following formalin injection. The initial nociceptive scores normally peaked 5 min after formalin injection (early phase) and 15-30 min. after formalin injection (late phase), representing both the neurogenic and inflammatory pain responses respectively.

Animals were treated i.p. with an aqueous solution of the tested compound (doses: 3, 10, 30 mg/Kg), 1 hour before the formalin injection. Control animals received only the vehicle.

In Table 8, the analgesic effect elicited in this test by a representative compound of Formula (I), is expressed as $ED_{50}$ both for the early and late phase, and compared with the performance of the standard reference, paracetamol.

TABLE 8

Licking Test

| Compound | Analgesic effect $ED_{50}$ (mg/Kg) | |
|---|---|---|
| | Early phase | Late phase |
| Example 1 | 19 | 13 |
| Paracetamol | 230 | 107 |
| Indomethacine | NE | 10 |
| Morphine | 4 | 4 |

NE: Not effective

The representative compound of the invention, compound of Example 1, demonstrated also in this test to be much more effective than Paracetamol in both the early and late phase of pain.

Pharmaceutical Compositions

Compounds of Formula I can be used in the manufacture of a suitable medication for the therapeutic treatment of pain and inflammatory related disorders. Especially for treatment of chronic pain disorders and immune-driven inflammatory events, which are a significant cause of many chronic inflammatory diseases where prolonged inflammation causes tissue destruction and results in extensive damage.

Accordingly, appropriate pharmaceutical composition of compounds of Formula (I), their salts and solvates thereof can be used for the treatment of acute and chronic pain, including but not limited to inflammatory pain and associated hyperalgesia and allodynia, osteoarthritis pain, postoperative pain, pain associated with metastatic cancer, trigeminal neuralgia, acute herpetic and post herpetic neuralgia, neuropathic pain, diabetic neuropathy.

In addition, appropriate pharmaceutical composition of compounds of Formula (I), their salts, and solvates thereof can be used for the treatment of immune-driven inflammatory events including but not limited to arthritis, inflammatory disorders of the gastrointestinal tract, inflammatory urinary bladder disorders, inflammatory disorders of the respiratory tract, inflammatory eyes disorders.

The compounds of the present invention may be administered orally, parenterally or topically, in a pharmacological effective amount. The term parenteral used herein includes intravenous, intramuscular, subcutaneous, intra-dermal and intra-articular.

For all methods of treatment herein discussed for the compounds of Formula (I), the daily oral dosage regimen will preferably be from about 0.1 to about 20 mg/Kg of total body weight. It will also be recognised by one of skill in the art that the optimal quantity and spacing of individual dosages of a compound of Formula (I) will be determined by the nature and extent of the condition being treated.

This invention also relates to a composition suitable for the treatment of the above diseases, containing a pharmaceutically effective amount of a compound of Formula (I), its salts, solvates and prodrugs thereof and its pharmaceutically acceptable carrier or diluent.

In order to use a compound of Formula (I) in therapy, it will normally be formulated into a dosage form in accordance with conventional methods of pharmacy and current guidelines and relevant good laboratory and manufacturing practices.

The preferred route of administration for the compounds of the invention is oral. The compounds of the invention can be formulated in a wide variety of oral dosage forms, such as capsules, tablets, pills, powders and dispersible granules. Suitable carriers can be one or more substances which may also act as diluents, flavouring agents, solubilizer, lubricants, suspending agents, binders.

Suitable carriers include but are not limited to magnesium carbonate, magnesium stearate, talc, lactose, pectin, dextrin, starch, methylcellulose, sodium carboxymethyl cellulose, cocoa butter and the like.

Techniques used to prepare oral formulations are the conventional mixing, granulation and compression or capsules filling. Other forms suitable for oral administration include emulsions, syrups and aqueous solutions. Emulsions can be prepare using emulsifying agents for example lecithin, propylene glycol or sorbitan monooleate. Aqueous solutions can be prepare by dissolving the active component in water and adding suitable colorants, flavours, stabilising agents.

The compounds of the present invention may be formulated for Parenteral administration (e.g., by injection or by continuous infusion) as a compostion with suitable carriers including aqueous vehicles solutions (i.e.: saline dextrose) or and/or oily emulsions. The drug product may be presented in unit dose forms, for example in ampoules or pre-filled syringes.

Formulation suitable for topical administration include liquid or semi-liquid preparations suitable for the penetration through the skin (e.g: liniments, lotions, ointments, creams and pastes) and drops suitable for administration to the eyes.

The invention claimed is:

1. A compound represented by Formula (I):

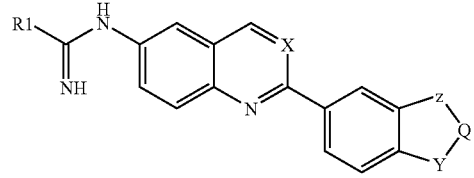

wherein:
- X is a nitrogen atom;
- Y and Z are independently selected from an oxygen atom (—O—); Q is $CHR_2$;
- R1 is independently selected from $C_1$-$C_4$ alkyl or $C_3$-$C_4$ cycloalkyl; the $C_1$-$C_4$ alkyl group being a linear or branched, saturated or unsaturated, hydrocarbon chain;
- $R_2$ is independently selected from $C_1$-$C_4$ alkyl and alkoxy (—$OR_1$); the compounds of formula (I) being either a free base form or a pharmaceutically acceptable salt thereof.

2. The compound according to claim 1 in the form of a pharmaceutically acceptable salt chosen from hydrochloride, hydrobromide, hydrogensulphate and sulphate, maleate, fumarate, oxalate, methanesulfonate, succinate, ascorbate, tartrate.

3. A pharmaceutical composition comprising, as active substance, at least one of the compounds according to claim 1, and further comprising pharmaceutically inactive ingredients selected from the group which consists of vehicles, binders, flavourings, sweeteners, disaggregants, preservatives, humectants and mixtures thereof.

* * * * *